United States Patent [19]

Sangha

[11] Patent Number: 5,334,502
[45] Date of Patent: Aug. 2, 1994

[54] METHOD OF COLLECTING, IDENTIFYING, AND QUANTIFYING SALIVA

[75] Inventor: Jangbir S. Sangha, Overland Park, Kans.

[73] Assignee: Osborn Laboratories, Inc., Olathe, Kans.

[21] Appl. No.: 814,077

[22] Filed: Dec. 24, 1991

Related U.S. Application Data

[63] Continuation-in-part of Ser. No. 800,647, Nov. 27, 1991, abandoned.

[51] Int. Cl.$^5$ .................. G01N 33/531; G01N 33/543
[52] U.S. Cl. .................. 435/7.21; 128/760; 128/769; 128/771; 604/1; 422/55; 422/56; 422/57; 422/59; 435/4; 435/5; 435/25; 435/28; 435/805; 435/967; 435/974; 436/164; 436/165; 436/169; 436/518; 436/528; 436/530; 436/805; 436/810
[58] Field of Search ............ 128/760, 769, 771; 604/1, 2; 422/55–58; 435/4, 14, 22, 25, 28, 805, 810, 7.21, 7.9, 7.92, 5, 974, 967; 436/164, 165, 169, 518, 528, 530, 805, 810, 901

[56] References Cited

U.S. PATENT DOCUMENTS

| | | | |
|---|---|---|---|
| 2,850,903 | 9/1958 | Schwerin | 128/771 |
| 3,319,621 | 5/1967 | Schwerin | 128/771 |
| 4,220,713 | 9/1980 | Rittersdorf et al. | 435/14 |
| 4,361,648 | 11/1982 | Shuenn-tzong | 435/10 |
| 4,762,917 | 8/1988 | Ikenaka et al. | 536/17.3 |
| 4,843,014 | 6/1989 | Cukier | 436/63 |
| 4,846,182 | 7/1989 | Fogt et al. | 436/125 |
| 4,945,043 | 7/1990 | Gerber | 436/537 |
| 5,024,935 | 6/1991 | McClune et al. | 436/518 |
| 5,166,053 | 11/1992 | Huguenel et al. | 435/967 |

OTHER PUBLICATIONS

*The Worthington Manual*, Chapter 1.11.1.7 Peroxidase, pp. 254–260.

Barbel Porstmann, T. Porstmann and Elsa Nugel, Comparison of Chromogens for the Determination of Horseradish Peroxidase as a Marker in Enzyme Immunoassy, *J. Clin., Chem. Clin. Biochem.*, vol. 19, 1981, pp. 435–439.

Kirk–Othmer, *Concise Encyclopedia of Chemical Technology*, article on Peroxides and Peroxy Compounds, Organic and an article on Hydrogen Peroxide, pp. 845–850 and p. 627.

C. J. Major, S. E. Read, R. A. Coates, A. Francis, B. J. McLaughlin, M. Millson, F. Shepherd, M. Fanning, L. Calzavara, D. MacFadden, J. K. Johnson and M. V. O'Shaughnessy, Comparision of Saliva and Blood for Human Immunodeficiency Virus Pervalence Testing, *The Journal of Infectious Diseases*, 1991; 163:699–702.

R. Haeckel and I. Bucklitsch, The Comparability of Ethanol Concentrations in Peripheral Blood and Saliva (The Phenomenon of Variation in Saliva to Blood Concentration Ratios), *J. Clin. Chem. Clin, Biochem.*, vol. 25, 1987, No. 4.

John C. Nucklow, The Use of Saliva In Therapeutic Drug Monitoring, *Therapeutic Drug Monitorying*, vol. 4, No. 3, 1982, pp. 229–247.

P. Holmstrom, S. Syrjanen, P. Laine, S–L. Valle and J. Suni, HIV Antibodies in Whole Saliva Detected by ELISA and Western Blot Assays, *Journal of Medical Virology*, 30:245–248 (1990).

Loren K. Thompson, David Yousefnejad, Karen Kumor, Michael Sherer and Edward J. Cone, Confirmation of Cocaine in Human Saliva After Intravenous Use, *Journal of Analytical Toxicology*, vol. 11, Jan./Feb. 1987, pp. 56–58.

Dr. James W. Paxton, Measurement of Drugs in Saliva: a Review, *Methods and Findings Exptl Clin Pharmacol* 1(1), 11–21 (1979).

Richard D. Kremer, Filter Paper in Clinical Diagnostic Screening, *Clinical Lab Products*, Oct. 1982 11(10):21–25.

*Primary Examiner*—Toni R. Scheiner
*Assistant Examiner*—Christopher L. Chin
*Attorney, Agent, or Firm*—Richard P. Stitt

[57] ABSTRACT

A method is provided for rapidly determining during a saliva specimen collection procedure the presence of an amount of saliva, and for verifying that the sample obtained is in fact saliva. Color indication by dye markers and/or enzymatic activation of color indicators provides an indication that at least a predetermined amount of saliva has been applied to an absorbent and the enzymatic reaction indicates that saliva is contained in the sample collected.

48 Claims, 2 Drawing Sheets fig. 1 fig. 7 fig. 8 fig. 9 fig. 10 fig. 11

METHOD OF COLLECTING, IDENTIFYING, AND QUANTIFYING SALIVA

This is a continuation-in-part application Ser. No. 07/800,647 filed Nov. 27, 1991, now abandoned.

CROSS-REFERENCE

Reference is made to the concurrently pending application of the present inventor, Jangbir S. Sangha, Ser. No. 07/814,080, now abandoned, relating to the associated apparatus for collecting and verifying the quantity and presence of saliva for dried saliva spot drug and HIV antibody testing.

BACKGROUND OF THE INVENTION

This invention relates to improvements in a method for collecting a saliva sample from human subjects. More particularly, the invention provides indication of the collection of a minimum saliva sample amount as well as providing verification that the sample collected is saliva. The indicator further serves to locate the saliva and to show the sample was properly applied to an absorbent after the saliva has been dried for shipping to a laboratory for HIV antibody testing or drug abuse testing or other viral or bacterial antibody testing, or testing for other analytes of interest.

In collecting body fluid samples, and in particular human body fluid samples, it is at times necessary to collect samples in the field or outside of a controlled collection environment. Two such cases are immediately evident, that of law enforcement sample collection for evidentiary purposes and the collection of samples by the health insurance industry for health status determinations on prospective insurance purchasers.

In law enforcement sample collection of human body fluid samples, the collection of saliva is potentially useful as a superior indicator of blood alcohol levels in contrast to simple "breathalizer" types of testing. Saliva samples can be saved for future confirmation of the original test results whereas the "breathalizer" tests cannot. For the health and life insurance industry saliva testing is useful as a matter of convenience for the individual seeking insurance. When the sample collection for testing for preexisting conditions can be conducted at their home or within their work site, inconvenience is minimized and there is less resistance to testing.

In the insurance industry it has become common practice to send out a medical on-site examiner and have the fluid sample—saliva—collected at a location most convenient for the subject desiring insurance. Heretofore on-site examiners have collected saliva by having individual expectorate into a container and then adding an anti-bacterial agent to the saliva and shipping it into the laboratory for testing or by collecting a sample of saliva on a swab and then plunging the swab into an anti-bacterial agent for shipment into the laboratory.

Inherent in such "on-site" sample collection situations is that subsequent transport of the sample to a testing laboratory is required. In many cases it is convenient, as well as necessary, to ship the sample to the laboratory by mail or courier in order to minimize the number of laboratory operations. In such cases it is beneficial if the sample can be reduced to a solid phase or at least minimized in volume. As a result it has recently been found advantageous to ship body fluid samples, blood in particular, as a dried spot on an absorbent matrix. In this manner the sample volume is reduced and the sample weight commensurately reduced by evaporation of the fluid component.

Conveyance of these physiological fluid samples to the laboratory often occurs under poor conditions and the use of public and private mail delivery or couriers to transport such samples increases the potential for careless handling. Damaged and leaking fluid samples may alarm or endanger courier or mail system workers who contact the damaged and leaking packages of fluid physiological materials. Thus it is of substantial benefit when the fluid component can be reduced or eliminated in such samples.

However, the application of the fluid sample to an absorbent upon which the sample can be dried causes certain problems in the case of saliva. Unlike the on-site examiner the receiving laboratory does not have the advantage of actual observation of the subject. Upon receiving an absorbent upon which a saliva sample has dried, the laboratory must be able to locate the saliva thereon (saliva being invisible unlike blood), determine that a sufficient quantity of the sample has been obtained to perform the tests to be conducted, and verify that the dried sample is, in fact, saliva and not another body fluid or a fake specimen. Once the sample is dried it may be easily transported to a laboratory where a wide range of tests may be performed on the sample.

A dried saliva spot on an absorbent may be used for determining drug use such as cocaine and may also be used for analyzing the health status of the potential insured for HIV antibodies or analytes of interest. The utility of saliva as a testing medium is a direct result of its formation in the body. Saliva is formed in the mouth by the salivary glands of the oral cavity and adjacent areas. The salivary glands consist of two parotid, submandibular and sublingual glands in addition to the labial and lingual glands as well as the small mucous glands of the soft and hard pallet. The daily saliva output is between 500 and 1,500 milliliters. This flow may be affected by various factors including age, sex, time of day, time of year, nutritional state and emotional state of the individual.

The main constituents of saliva are proteins, sodium, potassium, calcium, magnesium, chloride, bicarbonate, and inorganic phosphate. However, as the salivary gland ducts are separated from the human blood circulation by only a layer of epithelial cells many constituents of the blood are passed into the saliva. While most drugs and blood constituents seem to enter the saliva by diffusion across the epithelial cell lipid membrane, it is also possible that there is some active secretion into the saliva of drugs such as penicillin and lithium.

It has been confirmed that intravenous use of cocaine in addition to oral or intra-nasal administrations of cocaine may be determined from saliva. Recently, there has been interest in determining through saliva testing the presence of human immuno-deficiency virus (HIV) antibodies to assist insurance companies in screening out risks to business prior to offering contracts for health and life insurance.

Generally, samples of saliva for these purposes have been obtained by having the subject expectorate into a container. This is assisted by having or by having the subject suck or chew onto a washed rubber band, a piece of paraffin wax, chewing gum or a strip of citric acid-impregnated filter paper and then having the subject expectorate into a container or allowing the saliva to be absorbed onto an absorbent paper or sponge.

These saliva collection techniques, however, may be considered less than optimal for use in a business office situation where the form of collection may be obtrusive and out of keeping with the office environment. In addition, the sample must then be transported back to the testing laboratory and if the laboratory is some distance from the sample gathering location, the inconvenience and difficulty of shipping a body fluid sample is then incurred.

One avenue around these difficulties has been to allow the subject to place an absorbent swab or paper into the mouth and allow the absorbent material to become saturated with saliva within a set time. However, this presents the problem that it is difficult to determine the degree of saturation of the swab and if a number of saliva samples are being concurrently taken, it may not be possible for the on-site examiner to visually observe each subject and thereby personally witness and ascertain that it is saliva which has been absorbed onto the paper.

More importantly, due to the nature of the absorbent paper, it may be difficult for the on-site examiner to determine that adequate sample has been placed on the absorbent to allow proper testing. In this event it is necessary to return to the subject at a later date to collect an additional sample which is not only inconvenient but adds additional expense to the determination being made and may raise questions as to the competence of the company requesting the test, the competency of the on-site examiner, as well as the health of the subject.

Therefore, it is an object of the present invention to provide a method for field saliva sampling which will avoid the above debilities of the present methods of saliva sampling.

Another object is to provide a method for obtaining a saliva sample and determining as the sample is taken that an adequate sample has been obtained.

Yet another object of the present invention is to provide a field saliva sample collection method which can immediately verify that the sample obtained is in fact saliva.

Another object of the present invention is to provide a method for saliva sample taking which will at once indicate to the sample collector that a sufficient sample for testing has been collected and that the collected sample is in fact saliva.

Yet another object of the present invention is to provide a rapid and convenient method for saliva sample collection which can be conveniently and easily stored for law enforcement evidentiary purposes, It is yet another object of the present invention to provide a method for saliva sample collection which can be conveniently and easily shipped from one location to another.

Yet another object of the invention is to provide a method in which the area of application of a clear fluid sample may be observed after the sample is dried.

Yet another object of the invention is to provide a method that allows determination that the proper sample amount has been applied at the time of sampling as well as after the sample has been allowed to dry.

Yet another object of the invention is to provide a method which protects technical personnel working with a dried clear fluid sample by making apparent the location of the sample after it is dried.

Another object of the invention is to provide a method that indicates that the sample was correctly and uniformly applied to the absorbent.

Yet another object of the invention is to provide a method which can be made and utilized at a low cost.

Yet another object of the invention is to provide a method which assists in avoiding the need to take repeat samples from subjects due to improper sampling procedures.

Other objects and advantages of this invention will become apparent from the following description taken in connection with the accompanying drawings, wherein is set forth by way of illustration and example, an embodiment of this invention.

SUMMARY OF THE INVENTION

In broad summary, the method of the present invention takes advantage of the ability of the peroxidase enzyme in saliva, in the presence of a peroxide, to oxidize the "leuco" or colorless form of a dye or other indicator to produce a colored form of the dye or indicator. The reaction of the saliva peroxidase with the indicator may be used to determine that the sample is, in fact, saliva and also that sufficient sample has been placed on the absorbent.

A second enzymatic method for verification of saliva presence and sample sufficiency utilizes the amylase enzyme of saliva to effect a color change, from colorless to colored, in a substrate compound. The compound, a polysaccharide or oligosaccharide having a chromogenic moiety or molecule attached thereto, is applied to the absorbent at a location distant from the zone of application. Upon being contacted by the amylase of saliva the substrate reacts with the amylase to release the chromogen from the polysaccharide or oligosaccharide substrate to thereby provide a free chromogen which is colored and visible to an observer.

An alternate method relies on the application of a simple food dye placed at a particular predetermined distance from the zone of saliva application. The mixing effect of the saliva with the dye indicates that at least a predetermined amount of saliva has been placed on the absorbent.

Generally, the determination of adequate saliva absorption is accomplished by first determining the absorptive capacity of the selected absorbent. Once this is determined the proper position on the absorbent for application of the pre-positioned indicator may be selected. The proper position is that distance from the zone of saliva application which will require application and absorption of sufficient sample quantity for testing by the laboratory prior to the saliva contacting the indicator.

In this manner, once sufficient saliva has been absorbed so as to allow sufficient saturation of the absorbent to result in saliva contacting and reacting with the indicator, the on-site examiner can easily observe the color change of the indicator or the diffusing or migration of the indicator in the saliva and be assured that sufficient sample has been placed on the absorbent.

Other objects and advantages of this invention will become apparent from the following description taken in connection with the accompanying drawings, wherein is set forth by way of illustration and example, an embodiment of this invention.

DETAILED DESCRIPTION

The Collection Apparatus

Figures 1, 2, 3, 4, 5, 6:
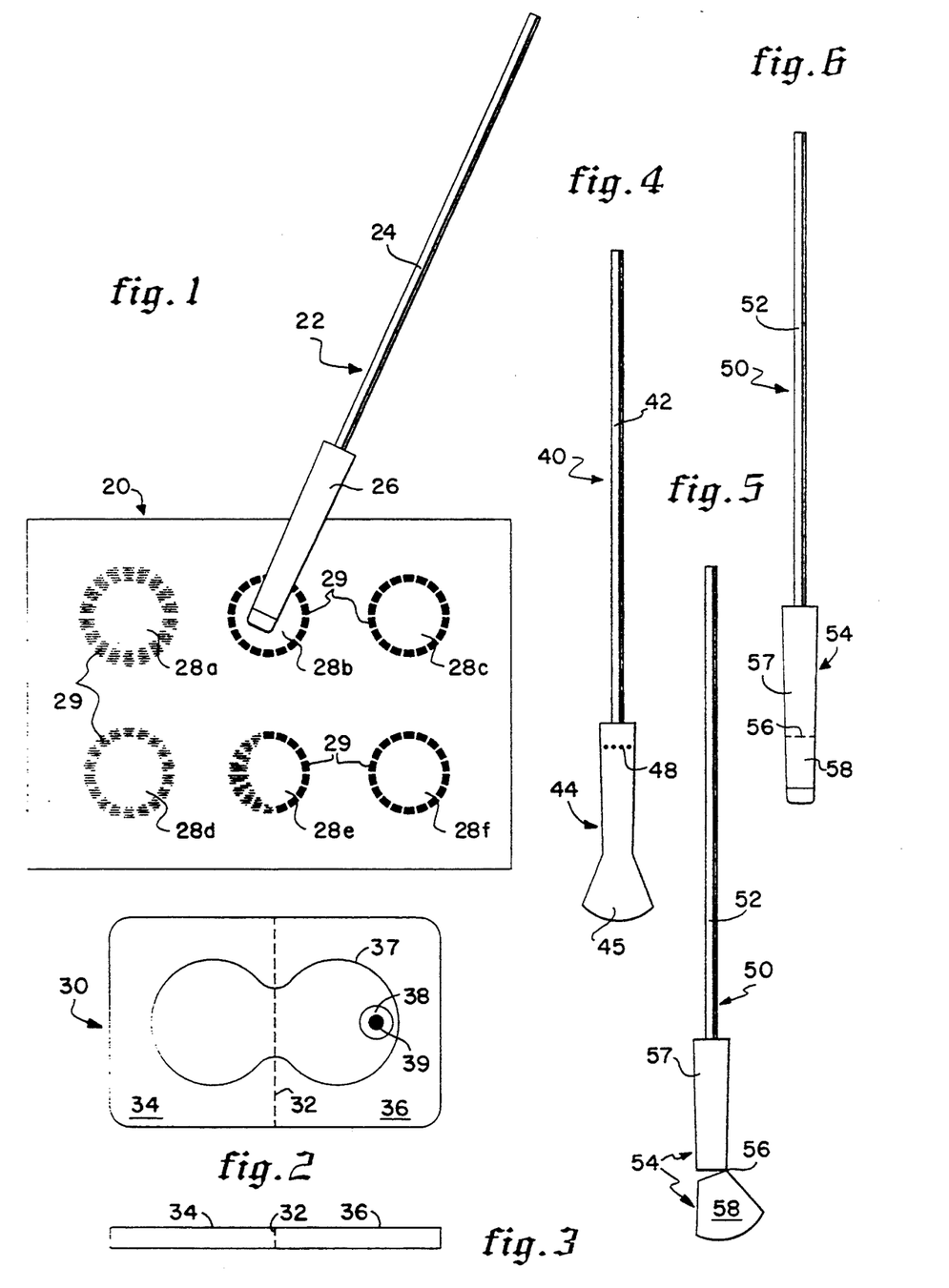
FIG. 1 is a plan view of the preferred embodiment showing an applicator transferring a saliva sample to the sample application zones of an absorbent layer. Each zone is shown surrounded by an indicator component, three of the indicators are shown in the migrated state after having been contacted by the applied saliva.
FIG. 2 is a plan view of an alternate embodiment showing an absorbent material bisected by perforations and having tandem indicator components one which surrounds the sample area and one isolated indicator for saliva verification.
FIG. 3 is a side elevational view of the embodiment of FIG. 2.
FIG. 4 is a front elevational view of an alternative embodiment of the apparatus with an absorbent material affixed to a handle and having an indicator component as a ring of dots around the upper most portion of the absorbent material.
FIG. 5 is a front elevational view of another embodiment of the invention showing a portion of the absorbent partially detached to allow separate testing with the indicator component.
FIG. 6 is a side elevational view of the absorbent swab of FIG. 5 with the detachable portion intact and the line of detachment shown in phantom lines.

In the embodiment of FIG. 1 sample probe 22 is utilized to obtain a saliva sample from a subject and then to apply the sample to an absorbent sheet or layer 20. Sample probe 22 is comprised of support stick 24 having swab 26 for saliva collection thereon. In use, swab 26 is placed into the mouth of a subject and saliva is collected. After collection of saliva on swab 26 probe 22 is removed from the subject's mouth and swab 26 is touched to saliva application zones 28a-f on absorbent sheet or layer 20. In this manner saliva is transferred from swab 26 onto absorbent layer 20.

In making the transfer of saliva, swab 26 is first touched to application zone 28a where saliva begins to be absorbed upon absorbent layer 20. As the saliva passes from swab 26 to absorbent layer 20 it diffuses through absorbent layer 20 and reaches indicator component 29. Indicator 29 is spaced a distance from the center of application zone 28a-f. The spacing is such that as saliva is absorbed onto absorbent layer 20 and migrates across absorbent layer 20 to contact indicator 29, it may be concluded that the proper quantity of saliva has been applied to absorbent layer 20 when indicator 29 reacts to the presence of the saliva. The on-site examiner can then proceed to each of the next zones until the complete sampling has been accomplished.

Indicator 29 of FIG. 1, as well as the other embodiments, may be either a vegetable dye or a colorless chemical substrate which acts as a chromogen in the presence of saliva. Where indicator 29 is a vegetable dye the contact of saliva with the vegetable dye at indicator 29 will cause some of the vegetable dye to begin to diffuse. This migration of the vegetable dye can be observed by the on-site examiner who is then assured that sufficient sample quantity has been collected to allow the testing laboratory to complete analysis of the saliva.

Alternatively, indicator 29 may be one of several compounds which becomes a colored chromogen in the presence of saliva. In this case, the saliva absorbs through layer 20 to contact indicator 29. Upon contact with the chromogen substrate in indicator 29 a color change in the indicator occurs. This color change shows the on-site examiner that the material on absorbent layer 20 is, in fact, saliva. In addition, the use of the chromogen at indicator 29 will simultaneously serve to indicate that sufficient saliva has been absorbed onto absorbent layer 20 at zone 28a-f to permit the laboratory to complete testing of the saliva sample. The chemical substrate enzyme reaction is more particularly discussed infra.

Once the sample has been applied to absorbent layer 20 the saliva sample spots are allowed to dry for shipping to the laboratory. By allowing the saliva spot to dry on the absorbent layer the saliva sample becomes more stable and can better withstand elevated temperatures. In addition, the cost of shipping the sample is substantially lowered as both weight and volume of the sample are diminished through evaporation of the excess fluid. The dried sample also offers added protection to laboratory personnel and shipping personnel as they do not have to deal with fluid samples which can spill or deal with leaking packages. The marker dye or chromogen substrate allows the laboratory technician to ascertain where the proper saliva sample was located so he or she can avoid contaminating the sample area and avoid the chance of infection. The sample obtained from the area within the marker will be uniform, therefore presenting a more accurate sample for analysis.

At the laboratory, portions of the dried saliva sample are punched from the absorbent and tested for HIV virus antibodies or drugs of abuse such as cocaine. Alternatively, the sample may be tested to identify tobacco smoking subjects through testing for nicotine and its metabolites or adducts in the saliva, or the dried saliva spot sample may be tested for other analytes of interest such as auto-antibodies, hormones, proteins, or drugs.

In using the simple dye marker method with the embodiment of FIG. 1, swab 26 contacts application zone 28b and in the fashion previously described saliva from swab 26 is transferred to application zone 28b. After a period of saliva transfer the saliva will contact indicator 29. Upon contact of the saliva with indicator 29 the dye indicator itself will begin to migrate in the absorbent layer 20. This is shown in application zone 28a of FIG. 1 where saliva, previously applied, has diffused partially into the absorbent layer. It is this migration or diffusion of indicator 29 which alerts the on-site examiner that sufficient saliva has been applied to absorbent layer 20.

Alternatively, where indicator 29 is composed of a colorless chromogen substrate which changes color upon contact by saliva, the colorless chromogen is incorporated into the apparatus at the location of indicator 29. As the substrate is colorless until it contacts saliva or saliva components, it is useful to mark the center of application zone 28a–f so the on-site examiner can apply the sample to the center of the zone 28a–f. Once the applied saliva contacts the indicator a chemical reaction with the enzymes present in saliva is initiated and the chromogen substrate is transformed into a visible colored compound.

The reaction which produces the color change in the chromogen is specific to the presence of saliva as opposed to water or other colorless fluids such as soft drinks. Thus it serves to indicate that the subject has properly saturated absorbent 20 with saliva and not with some other convenient fluid such as toilet water which would cause the simple dye marker indicator to change as described above.

In addition to indicating that the sample is saliva by the color change of the chromogen substrate, application of the dye or the chromogen in a pattern can provide additional information to the laboratory regarding the sample quality. It is intended that the on-site examiner apply the saliva to the center of the application zone. When this is the case the contacting of indicator 29 by the saliva will cause the dye, or the now colored chromogen, to migrate outwardly as shown in FIG. 1 at reference numeral 28a. The direction and degree of dye or colored chromogen migration will be a result of two factors: first, the accuracy with which the on-site examiner applied the sample to the center of the application zone; and second, the amount of sample applied to the zone.

As to application accuracy, if the on-site examiner applies the sample in the center of zone 28a–f, indicator 29 will be evenly contacted by saliva and the indicator will evenly migrate outwardly from the center of the application zone. Such an even outward migration may be observed at 28a or 28d. If the on-site examiner were to apply the sample outside of the indicator, the sample would migrate on absorbent 20 such that the indicator would flow inwardly toward the center of the zone of application as shown at application zone 28e. In this manner the laboratory can, by simple inspection determine if the sample has been properly applied. This opportunity to infer the point of sample application also imparts added safety to the work of the laboratory workers who must analyze the samples.

As workers, with the aid of the inventive indicator, can now see where the sample has been applied, they may avoid touching that part of the absorbent containing the sample. In the prior art absorbents, the laboratory technician was unable to observe the location of the colorless dried saliva and therefore could contact those areas containing sample which not only leads to erroneous results from manual contamination, but leads to infection of personnel.

The second attribute—observation of the amount of sample applied to the zone—is provided by noting the distance of outward migration of indicator 29. If the on-site examiner has applied the proper quantity of sample to application zone 28a–f a particular distance of migration of the indicator will result and can be observed by the on-site examiner at the time of sampling and by the laboratory personnel upon receipt. If the on-site examiner has applied an improper quantity of sample to the application zone the distance of migration by the indicator will be less than expected and a correction by the on-site examiner can be made by resampling or that zone can be avoided by the laboratory analyst at testing.

Referring now to FIGS. 2 and 3, another embodiment of the present invention is shown. In the embodiment of FIG. 2 absorbent sheet or layer 30 is bisected by perforations 32 into absorbent portions 34, 36. On one of absorbent portions 34, 36 is provided indicator 39 for determination of saliva presence. Indicator 39 is situated atop one-way barrier 38. One-way barrier 38 allows saliva to move upwardly from absorbent sheet or layer 30 to contact indicator 39, but does not allow the reversed migration of saliva which has become mixed with indicator 39 to then mingle with the saliva on absorbent layer 30. Referring to FIG. 3, a front side elevational view of the embodiment of FIG. 2 is illustrated having perforation 32 bisecting absorbent layer 30 into absorbent portions 34, 36.

In use, the embodiment of FIG. 2 is presented to a subject who is instructed to expectorate onto absorbent layer 30 in the vicinity of perforations 32. After several saliva samples are placed onto absorbent layer 30, the saliva will spread into both absorbent layer halves 34, 36. As saturation of absorbent layer 30 is completed the saliva will pass through one-way barrier 38 and contact indicator 39. Upon contact of indicator 39 with saliva the indicator will show the on-site examiner that saliva has approached that point on absorbent layer 30 and that sampling may be terminated.

Alternatively, the indicator in the embodiment of FIG. 2 may be placed at indicator 39 as well as perimeter indicator 37. In this situation it may be useful to utilize the simple vegetable or food dye marker for indicator 37 to indicate to the on-site examiner that there is a sufficiency of sample quantity while using the chemical substrate at indicator 29 as a means of indicating that the sample is in fact saliva.

Referring now to FIG. 4, another embodiment of the invention is shown. A sample probe 40 comprises a support stick 42 having an absorbent 44 attached to one end of support 42. A on-site examiner can, by grasping support 42, insert zone of application 45 into the mouth of a subject. Saliva from the subject is then wicked upwardly on absorbent 44 and diffuses through absorbent 44 toward support 42. Upon saturation of substantially all of absorbent 44, saliva will approach indicator 48. Again, indicator 48 may be a simple vegetable dye or it may be a chemical indicator of the type which will undergo a color change upon contact with saliva or components of saliva. In this manner the on-site examiner can observe when sufficient sample has been absorbed and/or verify that the sample is saliva by observation of the change in indicator 48.

Referring now to FIGS. 5 and 6, an alternate apparatus similar to that of FIG. 4 will be discussed. In the embodiment of FIG. 5 the entirety of absorbent 54 may be inserted into the mouth of a subject by support stick 52 for collection of saliva thereon. Thus, the entirety of absorbent 54 is the zone of application. After the collection of saliva, sample probe 50 is removed from the subject's mouth and testing of the sample can be accomplished to determine if the sample truly is saliva.

The indicator component of this embodiment is separate from the absorbent 54. Indicator test portion 58 of absorbent 54 is detached from sample portion 57 along perforations 56. After separation of test portion 58 from absorbent 54 the indicator component for saliva presence may be applied to test portion 58. If the test demonstrates that the sample on absorbent 54 is in fact saliva, sample portion 57 of absorbent 54, attached to support 52, may be allowed to dry and sent to the laboratory for testing for HIV antibodies or abuse of drugs such as cocaine or for testing of other analytes of interest such as islet cell antigen antibodies.

Referring to FIG. 6, a side elevational view of the embodiment of FIG. 5 is illustrated showing perforations 56 on absorbent 54 between test portion 58 and sample portion 57.

Figures 7, 8, 9, 10, 11:
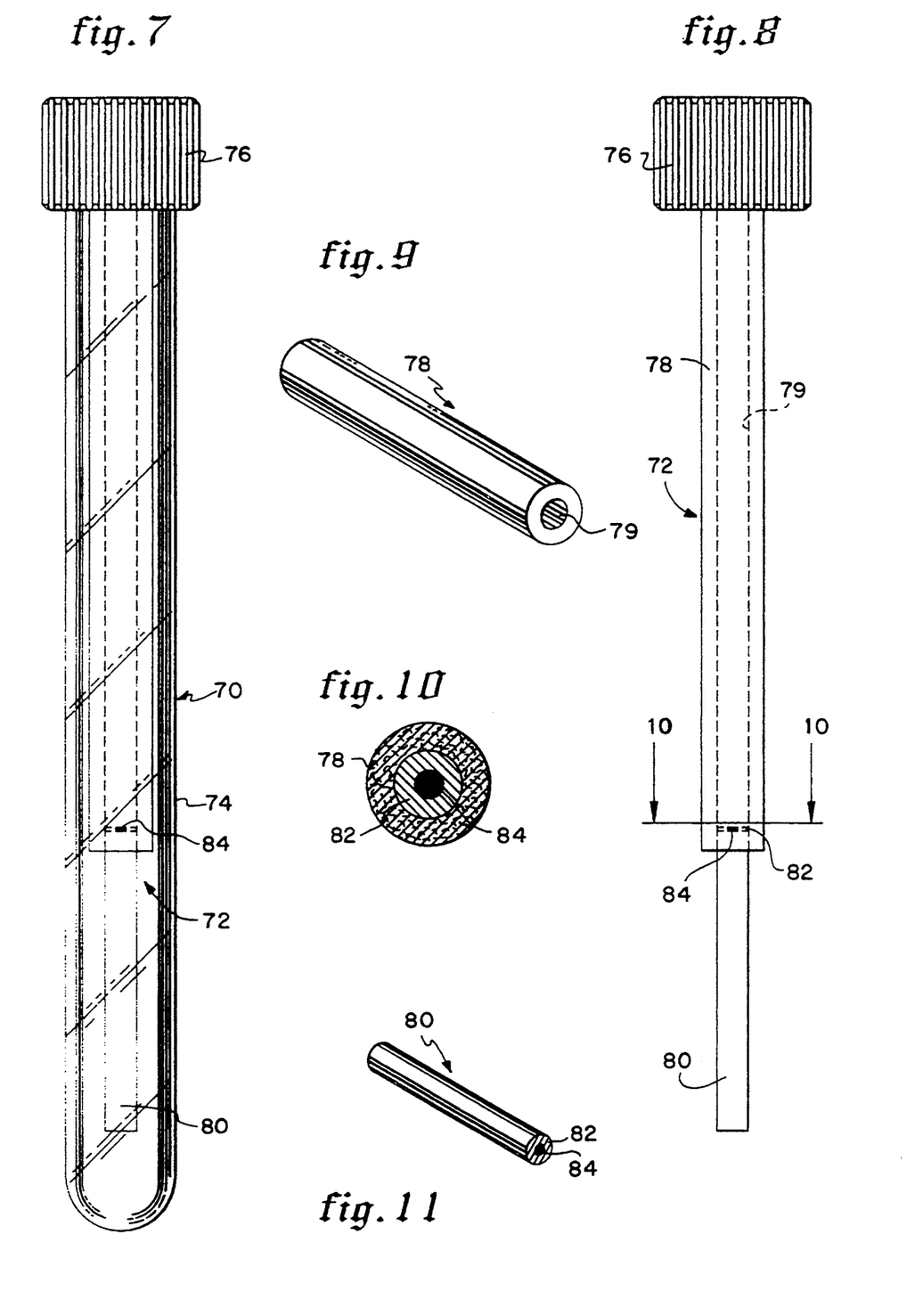
FIG. 7 is a side elevational view of yet another embodiment showing a sampling device within an outer protective tube.
FIG. 8 shows the sampling device of FIG. 7 withdrawn from the outer protective tube and showing the absorbent material extending from the base of the capillary tube connecting the absorbent to the cap.
FIG. 9 is a perspective view of the capillary tube showing the internal channel for insertion of the absorbent.
FIG. 10 is a plan view of the indicator component taken along line 10—10 of FIG. 8 and showing the indicator component on a one-way barrier on top of the absorbent material.
FIG. 11 is a perspective view of the absorbent material which is inserted into the capillary tube of the collection apparatus shown in FIG. 8 and showing on one end the one-way barrier and the indicator component.

Referring now to FIG. 7 another embodiment, collection device 70, is shown assembled for shipment. Sample probe 72 is contained within tube 74 to protect the sample probe during shipment. Probe 72 is secured within tube 74 by cap 76 which contacts tube 74 by a frictional fit or by registrable threads on tube 74 and cap 76. It is desirable that tube 74 be constructed from a light excluding material to protect the sample, the indicator and other components of collection device 70 from degradation by light exposure.

In FIG. 8, sample probe 72 is shown removed from tube 74. It may now be appreciated that in this embodiment cap 76 is joined to sample probe 72 and is utilized for holding sample probe 72 during sample collection. Attached to cap 76 of sample probe 72 is capillary tube 78. Capillary tube 78 extends from cap 76 approximately four to six inches. Absorbent or wick 80 is inserted into the end of capillary tube 78 opposite cap 76. In use sample probe 72 is inserted into the mouth of a subject and allowed to remain until such time as absorbent or wick 80 becomes saturated with saliva. The absorption of saliva onto absorbent 80 is assisted by capillary action provided by capillary tube 78.

Referring now to FIG. 9, a perspective view of capillary tube 78 is shown to illustrate hollow channel 79 which extends through tube 78 and into which absorbent 80 is inserted.

Referring now to FIG. 10, a cross-sectional view of sample probe 72 taken along line 10—10 of FIG. 8 is presented. Capillary tube 78 surrounds absorbent 80. On top of absorbent 80 is one-way barrier 82 and on one-way barrier 82 is indicator component 84. As saliva migrates or is wicked along absorbent 80 it approaches barrier 82 which is situated atop absorbent 80 as shown in FIG. 8. The saliva will pass through one-way barrier 82 to interact with indicator component 84. However, once the saliva has passed upwardly through barrier 82 to contact indicator 84 the saliva is unable to migrate back through barrier 82. Thus contact between the subject and the saliva that has interacted with indicator 84 is avoided.

Again indicator component 84 can interact with the presence of saliva in two ways. First, indicator 84 may be a simple dye marker which, when contacted by saliva, will become partially dissolved and then diffuse in a bleeding fashion. Such a change in the dye would indicate that saliva had entirely coated absorbent 30 and contacted indicator 84. The change in the dye marker indicator 84 serves to show the on-site examiner when a sufficient saliva sample has saturated absorbent 80 to allow testing to be properly accomplished at the laboratory.

A second function of indicator 84 is accomplished when a chemical chromogen substrate is incorporated into indicator 84. In this manner the apparatus provides rapid indication, at the time of taking a saliva sample from a subject, that not only has sufficient sample been applied to absorbent 80, but that the sample applied to absorbent 80 is, in fact, saliva. In FIG. 11, a perspective view of absorbent 80 is shown having barrier 82 and indicator 84 in place on an end of absorbent 80.

The Method of Indication of Sample Sufficiency

As outlined in the Summary of the Invention, the inclusion of a simple marker or dye which is at least partially soluble in saliva or which can migrate along the absorbent layer with the moving saliva front as it is wicked up the absorbent can provide a means for determining that a sufficient amount of saliva sample has been applied to the absorbent.

In this method, and referring now to FIG. 4, a simple dye or marker is placed on the absorbent layer as shown in FIG. 4 at reference numeral 48. This colored marker or dye need only be observable against the background of the absorbent 48. As the saliva saturates absorbent 44 in zone of application 45, the saliva will move along the absorbent and approach marker or dye 48 as the amount of saliva applied to absorbent 44 increases. This migration of a saliva front along absorbent 44 will eventually reach the point on the absorbent where marker or dye 48 has been applied. Upon contact of the saliva with marker or dye 48 an interaction between the saliva and the marker or dye will occur.

This interaction between the dye or marker and the saliva may be of various types. In the case where the dye or marker is soluble or partially soluble in saliva, the dye or marker will begin to diffuse into the saliva and the bleeding effect of the diffusing dye will be noted by the on-site examiner as illustrated in FIG. 1 at zones 28a, 28d.

Alternatively, if the dye or marker is insoluble in saliva but exhibits mobility with respect to its position on absorbent 44, 20, 30 such as colored fluorescent plastic micro particles, it is possible to accomplish the migration of the marker or dye along the absorbent with the migration of the saliva front along absorbent 44, 20, 30. This manner of utilizing a simple dye marker is suitable for indication to the on-site examiner that a sufficient level of saliva has been acquired on absorbent 44, 20, 37.

This signaling that sufficient saliva has been applied is accomplished by positioning marker or dye 48 (FIG. 4) or 29 (FIG. 1) or 37 (FIG. 2) at a predetermined position on the absorbent sufficiently distant from zone of application 28a–f, 35, 45 that the minimum quantity of saliva required for proper testing of the sample must be applied to zone of application 28a–f, 35, 45 prior to the saliva having sufficiently wetted absorbent 44, 20, 30, to come into contact with marker or dye 48, 29, 37. Thus, at the moment the dye or marker diffuses into the saliva or begins to move with the saliva front along absorbent 44, 20, 30 the on-site examiner is made immediately aware that sufficient quantity has been collected and sampling can cease.

In an alternate embodiment, not illustrated, a dye suitable for human consumption or external contact could be placed at a position on absorbent 44 (FIG. 4) below the known position at which sufficient sample is indicated. The dye is then allowed to migrate along absorbent 44 with the moving front of absorbed saliva. In this manner when the moving marker or dye front reaches the known point of sample sufficiency along absorbent 44 the on-site examiner would be aware that sufficient saliva sample had been collected.

In this embodiment, any of a number of suitable vegetable or food dyes may be used as the marker. Examples of suitable vegetable or food dye markers are the FDA approved dyes for use as food, drug or cosmetic dyes such as red No. 1 or No. 40 or yellow No. 5 or Blue No. 1 or a combination thereof or any other colorant which is non-toxic to humans. The dye or marker need only be easily visible against the absorbent selected and be safe for human consumption or human external contact.

In using the inventive apparatus it is necessary to first select the particular absorbent for collecting the saliva sample. Suitable examples of absorbents include an absorbent paper, S&S® 903 ™, manufactured by Schleicher & Schuell, Inc. or equivalent absorbents from other vendors such as Whatman, Inc. of Clifton, N.J. Also porous plastic absorbent supports formed from polyethylene, polypropylene, polyvinylidene flouride, ethylene-vinyl acetate, stryene-acrylonitrile, or polytetrafluoroethylene having known absorption characteristics may be used in place of cellulose or sponge material. As regards the absorbent, it is principally necessary that the material selected absorb a known reproducible quantity of saliva when it is provided with sufficient sample to saturate the material.

The amount of saliva required for accurate laboratory testing of the sample is then calculated. The amount of required sample in milliliters is divided by the number of milliliters of saliva which can be absorbed per square centimeter of absorbent material. The dye or marker is then imprinted upon the absorbent material at a location sufficiently distant from the area of sample application so as to require that at least the minimum necessary sample volume will be applied before the saliva interacts with the indicator. In this manner the desired degree of accuracy is assured.

By way of example and not limitation, it was determined that 300 microliters of saliva sample (wet volume) were required for conducting a particular series of laboratory tests on the saliva sample. The selected absorbent material was capable of absorbing 50 microliters of saliva per square centimeter of absorbent material. This resulted in a required total saturated absorbent area of four cubic centimeters to accomplish proper testing.

The design of the saliva sample apparatus is therefore a card of absorbent material provided with six saliva application zones 28a–f having a diameter of 1.25 cm and circumscribed by an imprinted dashed indicator line which encloses 1.23 square centimeters of absorbent area. Thus, if each zone is properly filled it will contain 61.36 microliters of saliva and the card will contain approximately 368 microliters of total saliva.

The on-site examiner is to apply the saliva to center of the application zone. As the saliva absorbs on the absorbent layer 20 (FIG. 1) it moves outwardly from the application zone and after application of slightly more than 50 microliters of saliva the saliva will contact the indicator. The contact of the saliva will cause the indicator to migrate outwardly with the moving saliva and will present the diffusion pattern shown in FIG. 1 at reference numeral 28a. If less than the required amount of saliva is applied to the card the saliva will only partially contact the indicator. In this case only a slight migration of the indicator will be noted and a diffusion pattern such as shown in FIG. 1 at reference numeral 28d will be observed.

Should the on-site examiner misapply the sample in place it outside the application zone this too will be noted. Such an application outside the zone would result in the saliva migrating inwardly—toward the center of the application zone as shown in FIG. 1 reference numeral 28e. In this case the on-site examiner would immediately note the improper application and a second application could be made. This therefore avoids the premature releasing the subject and the need to request that they return again for additional testing.

In the embodiment of FIG. 1, the application of the saliva to the absorbent card could be accomplished by having the subject expectorate into a container and then applying the saliva with a pipette to the absorbent sheet 20.

It will be apparent to those skilled in the art that a number of variations on this methodology and apparatus can be made. It is to be appreciated that such modifications of the embodiments shown are contemplated in the invention.

Method of Verification of Saliva Presence

As previously discussed, during the course of obtaining saliva samples either by law enforcement officers or by an on-site examiner for an insurance company or other interested party, it may be necessary to provide verification that the sample was in fact saliva. For law enforcement officers it may be necessary for evidentiary purposes to be able to swear that the sample obtained was observed to be saliva at the time of sampling. For on-site examiners of insurance companies it may be necessary for the on-site examiner to sample multiple subjects at one time resulting in diversion of the on-site examiner's attention from any single subject. The opportunity presented by non-observation could permit persons so disposed to substitute a water sample or some other clear fluid which would provide negative test results at the laboratory. The present method of verifying saliva presence avoids such attempts at substitution by reacting with components present in saliva to produce a reaction with an indicator which has been previously placed on the absorbent or which may be added to a portion of the absorbent after the sample has been collected.

One method of accomplishing the verification of saliva presence is through use of the salivary peroxidase (Myeloperoxidase) enzyme and/or catalase in saliva. The peroxidase of saliva is typical of most peroxidases in that it catalyzes the oxidation by hydrogen peroxide of a relatively narrow number of classes of organic compounds. These classes of compounds include phenols; aromatic, primary, secondary, and tertiary amines; the leuco-dyes; certain heterocyclic compounds such as ascorbic acid and indole; as well as certain inorganic ions such as the iodide ion.

It should be noted that the function of peroxidase is not restricted to hydrogen peroxide in particular, but that any number of compounds which are of the hydroperoxide type may act as the oxygen provider according to the following reaction scheme:

Peroxide + H$_2$O$_2$ ⟶ Compound I

Compound I + AH$_2$(oxidizable substrate) (colorless) ⟶

Compound II + AH°

Compound II + AH$_2$ ⟶ Peroxidase + AH°

2AH ⟶ Oxidized product(colored)

Some of the hydrogen peroxide compounds which may be utilized in this reaction are hydrogen peroxide, cumene hydroperoxide, benzoyl hydroperoxide, methyl hydrogen peroxide, ethyl hydrogen peroxide, and butyl hydrogen peroxide.

Alternatively, the peroxide necessary for the reaction with peroxidase or catalase may be generated in situ on the absorbent utilizing glucose oxidase on the absorbent to react with the glucose of the saliva sample to produce hydrogen peroxide. The generated hydrogen peroxide could then be utilized in reaction with the catalase or peroxidase of saliva to react with the colorless substrate compound to provide the inventive indicating system of the invention.

In the present invention the peroxidase and/or catalase of saliva is used to catalyze a reaction upon the absorbent which visibly indicates to the on-site examiner that the fluid sample obtained contains peroxidase and/or catalase and may be concluded to be saliva. Also, it may be indicated to the on-site examiner that sufficient sample has been collected for laboratory testing. The latter attribute is determined by the specific pre-positioning of the peroxidase/catalase substrate and reactants at a particular location on the paper as previously described for the simple marker methodology in determining sample sufficiency.

In the inventive method utilizing saliva peroxidase/catalase to verify the presence of saliva in a fluid sample, it is useful to employ an enzyme substrate which reacts with peroxidase/catalase to undergo an easily observed color change. A wide variety of such compounds exist and are well known in the art. In the present methodology the preferred class of enzyme substrate compounds for verification of saliva presence is known generally as the leuco-dyes or leuco compounds.

Leuco-dyes may be thought of as chromogens in that they will, in at least one of their molecular forms, become colored compounds easily observable in the visible spectrum. The classification "leuco" is due to the fact that these compounds present one molecular form which is white or colorless therefore exacting the name "leuco" dye (from the Greek leukos meaning clear) from observers.

Historically leuco-dyes have received much attention as vat-dyes for textiles. In this application the leuco form of the dye is soluble in alkalinic aqueous solutions whereas the colored or oxidized form of the compound is essentially insoluble. Once the textile has been saturated with the leuco form of the dye the textile is removed from the vat and air oxidized into the colored form of the compound.

It is this ability of these compounds to become colored upon oxidation which has been utilized in the inventive method to visibly indicate the presence of saliva. This is accomplished by relying on the reduction-oxidation (redox) reaction of the leuco-dyes to change from their colorless-reduced-('leuco') form into their colored-oxidized-form. The catalyst for performing this reaction is saliva peroxidase or saliva catalase which in the presence of an oxygen donor molecule such as a hydroperoxide can accept two hydrogen atoms from the leuco compound to thereby oxidize the leuco form enzyme substrate into its colored form.

This reaction is generally presented in the following equation:

n = 1: indigo, benzo-, naphtho- and anthraquinone
n = 2: anthanthrone, dibenzpyrenequinone, etc.
n = 4: pyranthrone, dibenzanthrone, dipyrazolanthrone, etc.

An alternate form of the leuco compounds is present in the aromatic amines and in particular derivatives of benzidine:

$R_1 = R_2 = H$    benzidine
$R_1 = CH_3$ and $R_2 = H$    o-tolidine
$R_1 = OCH_3$: $R_2 = H$    o-dianisidine
$R_1 = R_2 = CH_3$    tetramethylbenzidine (TMB)

The above reaction between the peroxidase of saliva and a hydroperoxide in the presence of a leuco dye proceeds generally as follows. Peroxidase joins with the hydroperoxide to provide an oxygen atom to the reactants which then acts as a hydrogen acceptor. The peroxidase-hydroperoxide complex then extracts two hydrogens from the leuco form of the molecule to oxidize the molecule to its colored form. In the case of amine compounds a hydrogen is extracted from each amine group to result in the tertiary amine. In the case of diols the hydrogen is removed from the two alcohol moieties to form the colored oxidized form of the compound and a molecule of water. Where hydrogen peroxide is used, two molecules of water are formed from the destruction of hydrogen peroxide.

Inventive use of this enzyme catalyzed reaction of leuco form enzyme substrate compounds into their oxidized colored form is accomplished by the application of the leuco form of the substrate compound in solution and application of a suitable hydroperoxide to a preselected location on an absorbent.

As previously described for the simple dye or marker method, the proper position for the leuco compound on the absorbent is determined by calculating the amount of saliva sample required for laboratory testing and then calculating the particular distance from a zone of saliva application for placement of the leuco compound. The proper distance is that which would require placement of sufficient saliva sample on the absorbent to saturate the absorbent to the preselected point to accomplish contact between the saliva and the leuco reactants.

The leuco substrate compound and the hydroperoxide compound are then applied to the absorbent at that location so that when saliva is wicked from the zone of application on the absorbent to the point of application of the leuco enzyme substrate and the hydroperoxide the peroxidase or catalase enzyme presence in saliva will contact the peroxide and the leuco compound substrate to oxidize the leuco substrate to its colored form. Thus is indicated the presence of saliva to the on-site examiner as well as indicating that a sufficiency of saliva sample had been applied to the absorbent.

By way of example, a solution of tetramethylbenzidine (TMB) dissolved in dimethyl formamide (DMF) or dimethyl sulfoxide (DMSO) to give a final concentration of 660 $\mu$grams/ml in an acetate buffer (0.05 mol/l) (pH 4.7 to 4.8) and containing 1 mmol/ml EDTA is applied to a preselected position (indicator 29) on absorbent layer 20 in FIG. 1. The TMB solution is then allowed to dry and a solution of cumene hydroperoxide in DMF (0.03 percent v/v) is then applied to the same area as was the TMB. After the peroxide has dried the absorbent layer 80 is protected from light. Alternatively, cumene hydroperoxide may be replaced by a 0.03% aqueous hydrogen peroxide solution in an acetate buffer (0.05 mol/l) containing 1 mmol/ml EDTA at a pH of 4.7 and dried immediately at elevated temperatures (50° C.±5° C.).

When an on-site examiner is prepared to take a sample the absorbent layer 20 (FIG. 1) is removed from the light protective cover and a sample probe 22 containing saliva from the subject is applied to the center of zone 28a FIG. 1. The swab is left in contact with absorbent layer 20 until the on-site examiner observes a color change as represented in FIG. 1 at indicator 28a. The swab 26 of probe 22 then may be removed from zone 28a and moved to zone 28b for application of saliva to that zone. In this manner the on-site examiner can quickly and conveniently deliver the required amount of saliva to the absorbent and also verify that, in fact, it is saliva which is being applied to the absorbent.

The saliva which has been applied to zone 28a migrates until it contacts the peroxide and the TMB. The peroxidase enzyme in the migrating saliva contacts the peroxide and TMB and oxidizes the TMB into its colored form whereupon the on-site examiner can observe the color change due to the reaction and determine that the sample is saliva and that the sample quantity was sufficient.

In a second example, a solution of o-phenylenediamine dissolved in DMSO to give a final concentration of 1 mg/ml in an acetate buffer (0.05 mol/l) (pH 4.7 to 4.8) and containing 1 mmol/ml EDTA is applied to a preselected position (indicator 29) on absorbent layer 20 in FIG. 1. The o-phenylenediamine solution is then allowed to dry and a solution of hydrogen peroxide in DMF (0.03 percent v/v) is then applied to the same area as was the o-phenylenediamine. After the peroxide has dried the absorbent layer 80 is protected from light. This is then utilized in the manner previously described.

In a third example, a solution of guaiacol dissolved in DMSO to give a final concentration of 50% v/v is applied to a preselected position (indicator 29) on absorbent layer 20 in FIG. 1. The guaiacol solution is then allowed to dry and a solution of hydrogen peroxide in acetate buffer, 0.05 mol/l, pH 4.7, 1 mmol /ml EDTA (0.03 percent v/v) is then applied to the same area as was the guaiacol. After the hydrogen peroxide has dried the absorbent layer 80 is protected from light. This is then utilized in the manner previously described.

In like manner this procedure can be accomplished with solutions of the below listed compounds at a concentration in a range of between 100 $\mu$grams to 1 milligram per milliliter dissolved in a suitable solvent such as an acetate buffer and organic solvent mixture (e.g. DMSO, DMF or alcohol). At this concentration the reaction of the leuco compound with peroxidase and the selected hydroperoxide will arrive at a sufficient end point (color change observation by the on-site examiner) within a period of 40 seconds to approximately ½ minutes.

Suitable leuco enzyme substrate and indicator compounds which can react in accordance with this method are benzidine; o-tolidine; o-dianisidine; o-phenylenediamine; 2,2'-azino-di(3-ethylbenzthiazoline sulphonic acid-6) (ABTS); 4-amino antipyrine; guaiacol; pyrogallol; 4-chloro-1-naphthol; and nitrotetrazolium blue chloride. It should also be appreciated that the buffers that can be utilized to maintain the pH of the peroxidase reaction (pH 4–7) may be citrate, succinate, phthalate or phosphate.

It will be appreciated by those familiar with the art of redox reactions that a number of additional compounds will be effective with the inventive method. It is to be understood that the substitution of such compounds for those particularly specified is contemplated within the present invention and will produce a method equivalent to that described herein.

As an alternative to reliance upon the peroxidase of saliva, the amylase enzyme of saliva may be utilized to produce a visible color change in a substrate compound. This color change is observable to the on-site examiner and indicates that the substance applied to the absorbent is saliva. Also, by placing the amylase-reactive compound at a specified distance from the zone of application, the on-site examiner can determine that sufficient sample has been applied to the absorbent to permit proper testing at the laboratory.

Amylase is present in all living organisms and in mammals is present in high concentration in saliva. Amylase is a member of the group of hydrolase enzymes which cleave the $\alpha$-1,4 glycoside bonds in oligosaccharides (from trisaccharides upwards) and polysaccharides such as starch, glycogen and dextrins. Amylase acts upon the $\alpha$-1,4-glucan links in large linear polysaccharides having three or more $\alpha$-1,4-linked D-glucose units. The high amylase activity in saliva can be used to drive a reaction which releases a portion of a polysaccharide substrate. If the released portion of the polysaccharide contains sufficient conjugated double bonds within its structure it will absorb light and be visible to an observer as a colored compound on the absorbent paper. It should be appreciated that in the present description the term polysaccharide embraces oligosaccharide and the two are used interchangeably when generally referencing an amylase substrate to which is attached a chromogen. Therefore the chromogen derivative reactive to amylase could be a tetraoside, pentaoside, hexaoside, heptaoside, or other polysaccharide.

In the inventive method, a colorless form of an amylase substrate (an oligosaccharide or a polysaccharide attached to a chromogen) in a proper combination of enzymes and buffer system is applied to an abosrbent and dried. Saliva is then applied to the absorbent by an on-site examiner. The substrate is then cleaved by the saliva amylase and enzymes present in the applied substrate solution to release the chromogen compound from the oligosaccharide. This results in a colored area on the absorbent paper to which saliva has been applied. This colored area is then visible to an on-site examiner or other observer.

The reactions by which amylase, in combination with other enzymes, cleaves the substrate molecule to release the the process of saliva on the absorbent. If the chromogen-containing oligosaccharide is placed at a particular distance from the zone of application the examiner may also determine that sufficient sample quality has been placed on the absorbent to permit analysis at the laboratory. In this manner the amylase present in saliva may be utilized within the inventive method and apparatus to determine both sufficiency of saliva quantity as applied to the absorbent and also verify that the substance applied to the absorbent is in fact saliva.

The substrate molecules utilized are generally composed of a polysaccharide or oligosaccharide chain having a chromogenic moiety or molecule attached to one end of the chain. The other end of the chain is either open or has attached a molecule which inhibits the enzymatic action of glucoamylase or α-glucosidase and therefore amylase. The purpose of such a blocking agent is to promote the action of amylase on the substrate molecule over the action of glucoamylase or α-glucosidase.

Examples of polysaccharide or oligosaccharide molecules having chromogens incorporated include: α-4-nitrophenylmaltoheptaoside, β-4-nitrophenylmaltoheptaoside, 4,6, ethylidine-blocked-4-nitrophenylmaltoheptaoside, silyl-blocked-4-nitrophenylmaltoheptaoside, 3-ketobutylidene-beta-2 chloro-4-nitrophenylmaltopentaoside, and derivatives of the above wherein Indole moiety is substituted for the p-nitrophenyl moiety such as Indolyl-α-D-maltoheptaoside. Also, saccharogenic substrates such as thiazine-labeled starches, amylopectin-azure and amylochrome dissolved in a suitable buffer may be used. However, if these substrates are used the eluate from the absorbent will require centrifugation to remove the substrate material.

In use within the inventive method a solution is composed of the chromogen-containing amylase substrate selected from the above compounds or their equivalents, α-glucosidase, glucoamylase, sodium chloride, calcium gluconate or calcium choride dissolved in a suitable buffer. Suitable buffers include: ACES (N-2-acetamido-2-aminoethanesulfonic acid), ADA (N-2-acetamidoiminodiacetic acid), BIS-Tris-Propane (1 3-bis[ins(hydroxymethyl)methylamino]propane), HEPES (N-2-hydroxyethylpiperazine-N'-2-ethanesulfonic acid}, HEPPS {N-2-hydroxyethylpiperazine-N'-3-propanesulfonic acid}, MES [2-{N-morpholino)ethanesulfonic acid], MOPS [3-{N-morpholino)propanesulfonic acid], PIPES [piperazine-N,N'-bis(2-ethanesulfonic acid)], TES [2{](tris-hydroxymethyl)methyl]amino}ethanesulfonic acid].

The following examples of this inventive method are presented by way of illustration and not limitation. The method first involves formulation of a solution containing the chromogen-linked substrate and secondary enzymes for release of chromogen is:

In the above reaction sequence the chromogen containing oligosaccharide (e.g. silyl-blocked-4-nitrophenylmaltoheptaoside) is first cleaved at the α-1,4 linkages to produce the chromogen linked to oligosaccharides of 2, 3 and 4 glucose units and oligosaccharides of 3, 4 and 5 glucose units. In the second step of the reaction glucoamylase and α-glucosidase further act on the chromogen-linked aligosaccharides of 2, 3 and 4 glucose units to hydrolase the chromogen from the 2 and 3 glucose unit oligosaccharides. A few of the 4 glucose unit oligosaccharides are also hydrolysed, but at a much slower rate. This hydrolysis results in release of a sufficient quantity of the chromogen to permit visual observation of a color presence on the absorbent by the on-site examiner.

Thus the examiner is able to quickly and easily verify the chromogen after action on the substrate molecule by amylase. In a first example, the solution applied to the substrate was composed as follows:

|  | Actual Amount Used Per 100 μl | Alternative Approximate Working Ranges Per 100 ml |
| --- | --- | --- |
| Silyl-blocked substrate (4-nitrophenylmaltoheptaoside) | 0.08 nM | 0.008–0.8 nM |
| α-Glucosidase | 3.0 units | 0.2–30 Units |
| Glucoamylase | 3.0 units | 0.1–30 Units |
| Sodium Chloride | 5.0 nM | 0.5 Nm–25 nM |
| Calcium Gluconate | 0.5 nM | 0.05 Nm–5 nM |
| PIPES buffer | 13.5 nM | 3.9 nM–40.5 nM |

Approximately 100 microliters of this solution was applied to the absorbent in the area of the saliva zone of application. The absorbent was allowed to dry prior to application of saliva thereto. Saliva was then applied to the absorbent and upon the saliva contacting the area to which the solution was applied, a yellow color was observed.

In a second example the following concentrations were used in formulating the substrate solution for application to the absorbent:

|  | Actual Amount Used Per 100 μl | Alternative Approximate Working Ranges Per 100 ml |
| --- | --- | --- |
| Amylase substrate (4-nitrophenylmaltoheptaoside PNPG-7) | 0.05 nM | 0.005 nM–0.5 nM |
| Sodium Chloride | 5.0 nM | 0.5 nM–25 nM |
| Calcium Chloride | 0.5 nM | 0.05 nM–5 nM |
| α-Glucosidase | 2.5 Units | 0.25 Units–25 Units |
| Glucoamylase | 1.0 Units | 0.1 Units–25 Units |
| PIPES buffer | 13.5 nM | 3.9 nM–40.5 nM |

Approximately 100 microliters of this solution are applied to the absorbent in the area of the saliva zone of application. The absorbent may be then allowed to dry prior to the application of saliva thereto. Saliva is then applied to the absorbent and upon the saliva contacting the area to which the solution was applied a yellow color will be observed.

Though the foregoing specific examples set forth the working concentrations of each ingredient, the concentrations may be varied according to the speed of the visual color reaction required.

When an on-site examiner is ready to utilize the absorbent containing the chromogen linked substrate, saliva is applied to the absorbent by any convenient method. Upon the amylase of saliva contacting the chromogen-linked substrate, the chromogen will be released from the remaining glucose units and become colored and visible to the examiner.

It is to be understood that while certain forms of this invention have been illustrated and described, it is not limited thereto, except insofar as limitations are included in the following claims.

Having thus described the invention, what is claimed as new and desired to be secured by letters patent is as follows:

1. A method of collecting and identifying saliva for analysis, said method comprising the steps of:
   (a) inserting a first absorbent element into the mouth of a subject for application of a fluid saliva specimen thereto,
   (b) providing a second absorbent element which is separate from said first absorbent element and having a zone of application for transfer of saliva thereto, wherein said zone of application comprises an indicator which indicates the presence of said fluid saliva specimen when contacted with said specimen, said indicator is spaced a predetermined distance from said zone of application to require transfer of a predetermined quantity of saliva to said second absorbent element prior to said applied saliva contacting said indicator, said predetermined distance also provides for collection of a sufficient quantity of specimen which is uncontacted by said indicator to permit subsequent analysis of said specimen,
   (c) transferring the fluid saliva from said first absorbent element to said zone of application, and
   (d) observing said indicator for saliva contact therewith in order to determine that said predetermined quantity of saliva has been transferred to said second absorbent element.

2. The method as claimed in claim 1, further comprising the steps of:
   (e) allowing said fluid saliva specimen to dry on said second absorbent element; and
   (f) utilizing said dried saliva to test for the presence of agents foreign to saliva and disease states.

3. The method as claimed in claim 1, wherein said indicator comprises:
   a peroxide; and
   a leuco dye for oxidation by interaction of said peroxide and the saliva such that a colored compound is produced to indicate the presence of saliva.

4. The method as claimed in claim 3, wherein said perioxide is selected from the group consisting of hydrogen peroxide, methyl hydroperoxide, ethyl hydroperoxide, isopropyl hydroperoxide, butyl hydroperoxide, benzoyl hydroperoxide and cumene hydroperoxide.

5. The method as claimed in claim 3, wherein said peroxide is produced by reaction of glucose oxidase with glucose, wherein said glucose oxidase is included in said indicator and said glucose is present in the saliva specimen.

6. The method as claimed in claim 3, wherein said leuco dye is selected from the group consisting of o-phenylenediamine, o-dianisidine, o-tolidine, guaiacol, 4-aminoantipyrine, pyrogallol, benzidine, tetramethyl benzidine, 4-chloro-1-naphthol and 2,2'-azino-di (3-ethylbenzthiazoline sulphonic acid-6).

7. The method as claimed in claim 1, wherein said second absorbent element comprises a sheet of material having a portion comprising said zone of application and upon which the applied fluid saliva specimen is dried, and wherein said indicator is positioned on said sheet in circumscribing relationship relative to said zone.

8. The method as claimed in claim 1, wherein said indicator comprises:
   a substrate reactive with an amylase enzyme of said saliva, said substrate having a portion thereof which upon reaction with said amylase presents visible color.

9. The method as claimed in claim 8, wherein said substrate is a polysaccharide having a chromogen attached thereto.

10. The method as claimed in claim 9, wherein said chromogen-containing polysaccharide is a p-nitrophenyl-containing polysaccharide.

11. The method as claimed in claim 9, wherein said chrmogen-containing polysaccharide is selected from the group consisting of α-4-nitrophenyl maltoheptaoside, β-4-nitrophenyl maltoheptaoside, 4,6 ethylidine-blocked-4-nitrophenylmaltoheptaoside, silyl-blocked-4-nitrophenylmaltoheptaoside, and 3-ketobutylidene-beta-2-chloro--4-nitrophenylmaltopentaoside.

12. The method as claimed in claim 9, wherein said chromogen-containing polysaccharide is an indole-containing polysaccharide.

13. The method as claimed in claim 9, wherein said chromogen-containing polysaccharide is selected from the group consisting of indolyl-α-maltoheptaoside; indolyl-β-maltoheptaoside; 4,6 ethylidine-blocked-indolyl maltoheptaoside; silyl-blocked-indolyl maltoheptaoside; 3-ketobutylidene-beta-2-chloro-indolyl maltopentaoside; and indolyl-α-D-maltoheptaoside.

14. A method of collecting for analysis, said method comprising the steps of:
   (a) providing an absorbent element having a zone of application thereon for insertion into a subject's mouth for absorption of saliva, said absorbent element being sized to extend out of the subject's mouth to provide an exterior absorbent element portion, wherein said exterior absorbent portion has an indicating means thereon which indicates the presence of saliva when contacted with saliva, said indicating means is positioned on said exterior absorbent element in sufficient spaced relationship to said zone of application to require application of at least a predetermined amount of said specimen to said absorbent element prior to the presence of the saliva being indicated, said spaced relationship further providing for collection of a sufficient quantity of saliva which is uncontacted by said indicator to permit subsequent analysis of the collected saliva,
   (b) inserting said zone of application into the mouth of a subject, (c) collecting a fluid specimen of saliva on said zone of application, (d) allowing said saliva to migrate on said absorbent from said zone of application to said exterior portion, and '(e) observing said indicating means for saliva contact therewith for determination that said at least predetermined quantity of saliva has been absorbed.

15. The method as claimed in claim 14, wherein said absorbent element comprises an elongated wick having an end portion comprising said zone of application.

16. The method as claimed in claim 14, wherein said means for indicating comprises a dye at least partially soluble in saliva such that contact therewith solubilizes the dye to indicate the presence of at least said predetermined amount of the specimen on said absorbent element.

17. The method as claimed in claim 16, wherein said indicating means is a vegetable dye.

18. The method as claimed in claim 16, wherein said indicating means is non-toxic to humans.

19. The method as claimed in claim 14, wherein said indicating means comprises saliva-insoluble, dyed or fluorescent micro particles which migrate with the specimen as it diffuses on said element to indicate the presence of at least said predetermined amount of the specimen.

20. The method as claimed in claim 14, wherein said means for indicating comprises:
a substrate reactive with an amylase enzyme of said saliva, said substrate having a portion thereof which upon reaction with said amylase presents visible color.

21. The method as claimed in claim 20, wherein said substrate is a polysaccharide having a chromogen attached thereto.

22. The method as claimed in claim 14, wherein said indicating means comprises:
a peroxide; and
a leuco dye for oxidation by interaction of said peroxide and the saliva such that a colored compound is produced to indicate the presence of saliva.

23. The method as claimed in claim 22, wherein said peroxide is produced by reaction of glucose oxidase with glucose, wherein said glucose oxidase is included in said indicating means and said glucose is present in the saliva.

24. A method of collecting and identifying saliva for analysis, said method comprising the steps of:
(a) applying a fluid specimen to an absorbent element having a sample portion and a separable test portion;
(b) providing a means for testing that upon contact with said specimen gives an indication of the presence of saliva in said specimen;
(c) following said step (a), removing said test portion from said sample portion; and
(d) applying said testing means to said test portion to contact the applied specimen, whereby the presence of saliva therein results in said indication and analysis may proceed utilizing said sample portion.

25. The method as claimed in claim 24, wherein said means for testing comprises:
a peroxide; and
a leuco dye for oxidation by interaction of said peroxide and the saliva such that a colored compound is produced to indicate the presence of saliva.

26. The method as claimed in claim 25, wherein said peroxide is selected from the group consisting of hydrogen peroxide, methyl hydroperoxide, ethyl hydroperoxide, isopropyl hydroperoxide, butyl hydroperoxide, benzoyl hydroperoxide and cumene hydroperoxide.

27. The method as claimed in claim 25, wherein said peroxide is produced by reaction of glucose oxidase with glucose, wherein said glucose oxidase is included in said indicator and said glucose is present in the saliva.

28. The method as claimed in claim 25, wherein said leuco dye is selected from the group consisting of o-phenylenediamine, o-dianisidine, o-tolidine, guaiacol, 4-aminoantipyrine, pyrogallol, benzidine, tetramethyl benzidine, 4-chloro-1-naphthol and 2,2'-azino-di (3-ethylbenzthiazoline sulphonic acid-6).

29. The method as claimed in claim 24, wherein said means for testing comprises:
a substrate reactive with an amylase enzyme of said saliva, said substrate having a portion thereof which upon reaction with said amylase presents visible color.

30. The method as claimed in claim 29, wherein said substrate is a polysaccharide having a chromogen attached thereto.

31. The method as claimed in claim 30, wherein said chromogen-containing polysaccharide is a p-nitrophenyl-containing polysaccharide.

32. The method as claimed in claim 30, wherein said chromogen-containing polysaccharide is selected from the group consisting of α-4-nitrophenyl maltoheptaoside, β-4-nitrophenylmaltoheptaoside, 4,6, ethylidine-blocked-4-nitrophenylmaltoheptaoside, silyl-blocked-4-nitrophenylmaltoheptaoside, and 3-ketobutylidene-beta-2 chloro-4-nitrophenylmaltopentaoside.

33. The method as claimed in claim 30, wherein said chromogen-containing polysaccharide is an indole-containing polysaccharide.

34. The method as claimed in claim 30, wherein said chromogen-containing polysaccharide is selected from the group consisting of indoly-α-maltoheptaoside; indolyl-β-maltoheptaoside; 4,6 ethylidine-blocked-indolyl maltoheptaoside; silyl-blocked-indolyl maltoheptaoside; 3-ketobutylidene-beta-2-chloro-indolyl maltopentaoside; and indolyl-α-D-maltoheptaoside.

35. A method of collecting from a subject a desired quantity of saliva sample for analysis comprising the steps of:
(a) providing a saliva collection absorbent comprising a zone for saliva application adapted for insertion into the subject's mouth and an absorbent indicator portion sufficiently spaced from said zone to position said indicator portion outside the mouth, said collection absorbent is attached to a handle which allows for uncontaminated manipulation of the absorbent and permits insertion of said zone for saliva application into the subject's mouth, said indicator portion has an indicator thereon which signals the presence of saliva on said indicator portion of said absorbent and said indicator spaced a predetermined distance from said zone to permit collection of a predetermined amount of saliva prior to contact of the collected saliva with said indicator, said predetermined distance providing for collection of a sufficient quantity of specimen which is uncontacted by said indicator for subsequent analysis of the collected saliva sample,
(b) inserting said application zone into the subject's mouth for saliva collection, (c) allowing saliva to absorb onto said zone and migrate toward said indicator, (d) observing said indicator during saliva collection to determine saliva contact with sad indicator, and (e) withdrawing said zone from the mouth upon indicator reaction with the saliva.

36. The method as claimed in claim 35, wherein said indicator comprises:

a peroxide; and a leuco dye for oxidation by the interaction of said peroxide and the saliva such that a colored compound is produced to provide said indication.

37. The method as claimed in claim 36, wherein said peroxide is selected from the group consisting of hydrogen peroxide, methyl hydroperoxide, ethyl hydroperoxide, isopropyl hydroperoxide, butyl hydroperoxide, benzoyl hydroperoxide and cumene hydroperoxide.

38. The method as claimed in claim 36, wherein said peroxide is produced by reaction of glucose oxidase with glucose, wherein said glucose oxidase is included in said indicator and said glucose is present in the saliva.

39. The method as claimed in claim 36, wherein said leuco dye is selected from the group consisting of o-phenylenediamine, o-dianisidine, o-tolidine, guaiacol, 4-aminoantipyrine, pyrogallol, benzidine, tetramethyl benzidine, 4-chloro-1-naphthol and 2,2'-azino-di (3-ethylbenzthiazoline sulphonic acid-6).

40. The method as claimed in claim 35 wherein said handle comprises:

a hollow tube adapted for insertion of said absorbent indicator portion therein, and means on said tube for allowing observation of saliva contact of said indicator on said absorbent.

41. The method as claimed in claim 40 wherein said means for allowing observation comprises an opening in said tube to permit observation of said indicator containing portion of said absorbent.

42. The method as claimed din claim 35 further comprising the step of: marking said collected saliva sample to correlate the subject's identity with the collected saliva sample.

43. The method as claimed din claim 35, wherein said indicator comprises:

a substrate reactive with an amylase enzyme of said saliva, said substrate having a portion thereof which upon reaction with said amylase presents visible color.

44. The method as claimed in claim 43, wherein said substrate is a polysaccharide having a chromogen attached thereto.

45. The method as claimed in claim 44, wherein said chromogen-containing polysaccharide is a p-nitrophenyl-containing polysaccharide.

46. The method as claimed in claim 44, wherein said chromogen-containing polysaccharide is selected from the group consisting of α-4-nitrophenyl maltoheptaoside, β-4-nitropehnyl maltoheptaoside, 4, 6 ethylidine-blocked-4-nitrophenylmaltoheptaoside, silyl-blocked-4-nitrophenylmaltoheptaoside, and 3-ketobutylidine-beta-2-chloro-4-nitrophenylmaltopentaoside.

47. The method as claimed in claim 44, wherein said chromogen-containing polysaccharide is an indole-containing polysaccharide.

48. The method as claimed in claim 44, wherein said chromogen-containing polysaccharide is selected from the group consisting of indolyl-α-maltoheptaoside; indolyl-β-maltoheptaoside; 4, 6 ethylidine-blocked-indolyl maltoheptaoside; silyl-blocked-indolyl maltoheptaoside; 3-ketobutylidine-beta-2-chloro-indolyl maltopentaoside; and indolyl-α-D-maltoheptaoside.

* * * * *